United States Patent [19]

Obenaus et al.

[11] Patent Number: 4,517,395

[45] Date of Patent: May 14, 1985

[54] PROCESS FOR THE SELECTIVE HYDROGENATION OF POLYUNSATURATED HYDROCARBONS IN HYDROCARBON MIXTURES

[75] Inventors: Fritz Obenaus; Franz Nierlich; Otto Reitemeyer; Bernhard Scholz, all of Marl, Fed. Rep. of Germany

[73] Assignee: Chemische Werke Huls Aktiengesellschaft, Marl, Fed. Rep. of Germany

[21] Appl. No.: 438,465

[22] Filed: Nov. 2, 1982

[30] Foreign Application Priority Data

Nov. 4, 1981 [DE] Fed. Rep. of Germany ....... 3143647

[51] Int. Cl.$^3$ ............................ C07C 5/03; C07C 5/08
[52] U.S. Cl. .................................. 585/259; 585/260; 585/261; 208/143
[58] Field of Search ................ 585/259, 260, 261; 208/143

[56] References Cited

U.S. PATENT DOCUMENTS

| | | | |
|---|---|---|---|
| 3,325,556 | 6/1967 | De Rosset et al. | 585/261 |
| 3,674,886 | 7/1972 | Komatsu et al. | 585/261 |
| 3,743,684 | 7/1973 | Johnson et al. | 585/261 |
| 3,842,137 | 10/1974 | Libers et al. | 585/259 |
| 3,912,789 | 10/1975 | Frevel et al. | 585/259 |
| 4,020,119 | 4/1977 | Johnson et al. | 585/259 |

FOREIGN PATENT DOCUMENTS 1184336 12/1964 Fed. Rep. of Germany .

*Primary Examiner*—Delbert E. Gantz
*Assistant Examiner*—Anthony McFarlane
*Attorney, Agent, or Firm*—Antonelli, Terry & Wands

[57] ABSTRACT

A process for the selective hydrogenation of hydrocarbons having three and more carbon atoms and several double bonds or with triple bonds in monoene-containing hydrocarbon mixtures is described. These compounds are selectively hydrogenated to monoenes in a practically quantitative fashion. Before beginning the hydrogenation, a small amount of carbon monoxide and once to twice the stoichiometric quantity of hydrogen are homogeneously dissolved in the hydrocarbon mixture. The mixture is hydrogenated as a homogeneous liquid phase on a fixed palladium catalyst under a moderately high pressure and at a moderately high temperature. No isomerization can be found in the monoenes and no side reactions or secondary reactions occur.

12 Claims, No Drawings

PROCESS FOR THE SELECTIVE HYDROGENATION OF POLYUNSATURATED HYDROCARBONS IN HYDROCARBON MIXTURES

BACKGROUND OF THE INVENTION

The invention relates to a process for the selective hydrogenation of hydrocarbons (HC) containing three or more carbon atoms and having conjugated and/or cumulative double bonds and/or acetylenic triple bonds in monoene-containing mixtures of hydrocarbons having at least three carbon atoms in the liquid phase on fixedly disposed catalysts. Such HC mixtures are produced, for example, when processing mineral oil.

Prior to the further processing of such hydrocarbon mixtures, it is frequently necessary to free the mixtures of polyunsaturated and acetylenic compounds. It is expedient to hydrogenate these compounds. The invention has the purpose of rendering hydrogenation selective to avoid to a maximum extend any losses of monoenes by the formation of saturated hydrocarbons and, in some cases, by rearrangement into undesired, unsaturated isomers. The term "monoenes" as used herein refers to mono-ethylenically unsaturated compounds; i.e., compounds having a single double bond.

Such hydrogenations can be conducted by means of conventional fixed catalysts. Especially suitable are metals of group VIII and the first subgroup of the Periodic Table applied, for example, to pumice, clays, or silicates as the support material. Several processes are known wherein the selectivity is raised by chosen reaction conditions or by modification of the catalyst.

Advantageous methods are the "cold hydrogenation" at a relatively low temperature (German Pat. No. 1,568,542); the hydrogenation in the liquid phase with dissolved hydrogen (British Pat. No. 1,122,018), and the hydrogenation of dienes to monoenes on palladium catalysts in the presence of ammonia (Belgian Pat. No. 802,721).

It has, furthermore, been suggested to modify the catalysts with sulfur compounds. Thus, it is possible to obtain catalysts by treatment with thioethers, for example, which act selectively on the hydrogenation of acetylene (French Pat. No. 1,240,175). Catalysts doped with hydrogen sulfide are suitable for the selective hydrogenation of butadiene; however, they catalyze simultaneously the isomerization of, for example, butene-1 to butene-2 (French Pat. No. 2,355,792).

Also, the addition of carbon monoxide in small amounts catalyzes the isomerization of butene-1 to butene-2 in the presence of hydrogen on palladium catalysts (French Pat. No. 2,438,084).

The conventional methods are unsatisfactory, since a certain proportion of the unsaturated hydrocarbons in the hydrocarbon mixture is entirely hydrogenated and, in many cases, isomerization cannot be prevented. In the hydrogenation of butadiene in mixtures made up of $C_4$-hydrocarbons, for example, butene-1 is isomerized to butene-2.

There is, thus, the objective to develop a simple process for the selective hydrogenation of hydrocarbons having conjugated and/or cumulative double bonds and/or acetylenic triple bonds in monoene-containing mixtures of hydrocarbons having at least three carbon atoms; i.e., from 3 to 5 carbon atomes in the liquid phase on fixedly arranged catalysts, wherein the hydrogenated compounds are converted into monounsaturated compounds and are retained as such and, furthermore, wherein no isomerization of the monoenes occurs.

SUMMARY OF THE INVENTION

This objective has been attained according to the invention by a process having the following characterizing features and procedures:

adding hydrogen to the hydrocarbon mixture to be hydrogenated, in a finely divided form and in such quantitative ratios that in all cases a homogeneous liquid phase is obtained before the hydrocarbon mixture enters the hydrogenation zone, which quantitative ratios are stoichiometrically sufficient at least for the hydrogenation of the polyunsaturated as well as the acetylenic compounds to the corresponding monoenes;

adding carbon monoxide to the hydrocarbon mixture to be hydrogenated, in a finely divided form, wherein, in all cases, a homogeneous liquid phase is obtained before the hydrocarbon mixture enters the hydrogenation zone, and wherein the proportion of carbon monoxide amounts to at least 0.05 weight ppm—based on the weight of the hydrocarbon mixture;

passing the thus-composed reaction mixture in the liquid phase over a fixedly arranged catalyst with 0.01 to 3 weight % of palladium, based on the weight of the support.

A homogeneous liquid phase exists on the catalyst, not a gaseous phase; in other words, hydrogen ($H_2$) and carbon monoxide (CO) are completely dissolved in the HC mixture to be hydrogenated. $H_2$ and CO are completely dissolvable in HC mixtures as long as the concentration is below 1%.

DETAILED DESCRIPTION OF THE INVENTION

The stoichiometric $H_2$ quantity is that which, by calculation, is required for converting the polyunsaturated and the acetylenic compounds into the corresponding monoenes. This quantity can be calculated from the composition of the hydrocarbon mixture to be hydrogenated.

The minimum amount of CO to be based on the amount of the hydrocarbon mixture is determined empirically, by increasing, stepwise, the addition of CO, reacting an at least stoichiometric amount of $H_2$, and measuring, in each case, the concentration of the desired monoenes after the hydrogenation. The minimum amount of CO is that at which, under the selected hydrogenation conditions, the concentration of the desired monoenes in the hydrogenated HC mixture has reached its maximum. The sequence of addition of $H_2$ and CO is optional. Even a suitable blend of these gases can be added. The desired monoenes can be, in a mixture of $C_3$-hydrocarbons, propene; in case of hydrocarbons of four and more carbon atoms, one of the monoene isomers, or the sum thereof.

With the use of a constant quantity of $H_2$, the minimum amount of CO increases with the palladium content of the catalyst and with the hydrogenation temperature. If the amount of $H_2$ is increased for practical reasons, then the quantity of CO must, likewise, be raised.

Exceeding the minimum amount of CO does not alter the result of the selective hydrogenation. The upper limit value of the CO quantity is attained if the gaseous CO no longer dissolves completely in the HC mixture to be hydrogenated; i.e., if a heterogeneous mixed phase of gas and liquid is formed on the catalyst.

The amount of CO based on the mass of the hydrocarbon mixture is at least 0.05 ppm by weight. Dosages of above 20 ppm by weight no longer improve, as experience has shown, the results attainable under the other selected conditions. The process of this invention is not linked to any specific palladium catalyst. The catalyst contains 0.01–3% by weight of palladium, preferably 0.1–2% by weight.

The catalyst supports are to be inert; i.e., they are not to impair the selective hydrogenation. Among such supports are, for example, aluminum oxide ($Al_2O_3$), silica gel and activated carbon.

The remaining parameters of the hydrogenation; namely, reaction temperature, reaction pressure, concentration of the components in the HC mixture to be hydrogenated, type of admixing of $H_2$ and CO to the HC mixture, and throughput of HC mixture, exert a subordinate influence on the process of this invention.

The reaction temperature is significant for the process of this invention only insofar as the minimum amount of CO rises with the temperature. On account of the high reaction rate, the selective hydrogenation is also possible at low temperatures. The lower limit of the reaction temperature is primarily determined by practical reasons of no importance for the subject of this invention.

In case of aqueous hydrocarbon mixtures, the lower reaction temperature will be at about 0° C. The upper limit of the reaction temperature is determined by the critical data of the hydrocarbon mixture before and after hydrogenation; these are, for example, for propene, 91.9° C. and 4.5 MPa (MPa=mega-Pascal). Thus, the upper limit of the reaction temperature is, for example, in the presence of propene at about 90° C. If the hydrogenation is to take place at a high temperature, the apparatus must be designed for the corresponding pressure. Under practical conditions, a temperature of between 10° C. and 75° C. is preferred.

The reaction pressure has only an indirect effect on the process of this invention. The pressure must be sufficiently high to preserve the liquid phase at the catalyst. The pressure can be raised if the quantities of $H_2$ and CO to be dissolved are to be increased. In general, a reaction pressure is used of about 1.5 MPa; 6 MPa will be exceeded only in rare instances. The liquid phase on the catalyst can be preserved for all mixture compositions by the choice of a suitable reaction pressure and a suitable reaction temperature.

If the $H_2$ concentration required is too high to obtain complete dissolution in the hydrocarbon mixture at the desired reaction conditions, then the hydrocarbon mixture can be hydrogenated in two or more stages, or the hydrogenated hydrocarbon mixture can re recirculated, in part.

Several examples for hydrocarbon mixtures suitable as the starting material are compiled in Tables 1 and 2.

The hydrocarbon mixture to be hydrogenated is combined with finely divided $H_2$ and CO according to one of the known methods, so that the gases are dissolved faster.

The throughput of hydrocarbon mixture to be hydrogenated through the reactor is within the range customary for hydrogenation reactions of 5–300 liters of hydrocarbon mixture per liter of catalyst volume and hour.

The composition of the hydrocarbon mixture prior to and after the hydrogenation is preferably determined by gas chromatography. Conversion and isomerization are calculated from the changes in the concentrations of the components.

It is surprisingly possible by means of the process of this invention to quantitatively hydrogenate the polyunsaturated and acetylenic compounds to the corresponding monoenes; namely, with the use of merely the stoichiometric amount of $H_2$. The residual content of polyunsaturated and acetylenic compounds in the hydrocarbon mixture then is close to the detection limit after the selective hydrogenation. The originally existing monoenes and the monoenes formed during the selective hydrogenation remain unaltered during the selective hydrogenation. This is surprising, especially in view of the teaching in French Pat. No. 2,438,084.

The process of this invention has the following advantages:

The compounds to be hydrogenated are selectively hydrogenated in a practically quantitative fashion.

The monoenes are not hydrogenated to saturated compounds; in this connection, it makes no difference whether the monoenes were present in the hydrocarbon mixture before hydrogenation or have been formed by the hydrogenation.

The hydrogenation is selective within a very large range of concentration of the polyunsaturated and acetylenic compounds.

There is no detectable isomerization of the monoenes; for example, butene-1 is not isomerized to butene-2.

The catalyst attains the desired selectivity immediately in the presence of the minimum CO quantity.

No special purity requirements need to be met by the hydrocarbon mixture to be hydrogenated or by the gaseous $H_2$ and CO, as long as the minimum amount of CO and the stoichiometric quantity of $H_2$ are maintained, and the secondary components do not represent catalyst poisons.

Water dissolved in the hydrocarbon mixture does not interfere. The minimum CO quantity can even be somewhat reduced in the presence of dissolved water.

Since selectivity is preserved even at a higher reaction temperature, no expensive cooling devices or refrigerating plants are necessary for the process of this invention.

Since, besides the desired reactions, there are no secondary or consequent reactions, no additional heat effects occur, whereby heat removal is simplified.

The metered feeding of the quantities of $H_2$ and CO can be easily regulated with automatically operating analytical methods.

The process of this invention makes it possible, for example, to obtain butene-1 in a quality suitable for polymerizations by distillation from $C_4$-hydrocarbon mixtures containing, besides butene-1, also butadiene and acetylenic compounds. Residues of excess $H_2$ and the CO dissolved in the hydrocarbon mixture, according to this invention, do not interfere in this procedure.

The invention will be explained, with reference to the following examples, without being limited thereto.

Composition of the Hydrocarbon Mixture to be Hydrogenated and Hydrogenation Conditions Hydrocarbon mixtures having the composition indicated in Table 1 and Table 2 are utilized for the following examples. Moreover other hydrocarbon mixtures containing monoenes with three to five carbon atoms simultaneously can be used for selective hydrogenation. The concentration is set forth in weight % or ppm by weight and is based on the amount of hydrocarbon mixture. Additionally, the required stoichiometric $H_2$ concentration, based on the content of the polyunsaturated and acetylenic compounds, is indicated.

Although the stoichiometric amount of $H_2$ is adequate for selective hydrogenation, a somewhat higher $H_2$ concentration is generally chosen in order to compensate for fluctuations in the concentration of the compounds to be hydrogenated.

After adding the amounts of $H_2$ and CO, respectively recited in the examples, which amounts are dissolved in the hydrocarbon mixture, the hydrocarbon mixture is hydrogenated under the indicated conditions as a liquid phase on a fixedly arranged palladium catalyst on an inert support. The throughput is set forth in liter of hydrocarbon mixture per liter of catalyst volume and hour.

COMPARATIVE EXAMPLE

Hydrogenation Without Addition of CO

In the hydrocarbon mixture shown in Table 1, somewhat more than the stoichiometric quantity of $H_2$ is dissolved, in one instance (Example A), and about twice this amount is used in the other instance (Example B). The mixture (water content < 5 ppm) is hydrogenated under the following conditions:

Temperature 21° C.
Throughput 35 liter/liter·hour
Pressure 1.3 MPa
Catalyst 0.5% Pd on $Al_2O_3$ The following result was obtained:

|  |  | HC Mixture Contains | | | | |
|---|---|---|---|---|---|---|
|  |  | Butadiene ppm | Butyne ppm | Butenyne ppm | Butene-1 % abs. | Δc % rel |
| Before Hydrogenation |  | 1960 | 56 | 12 | 48.4 | — |
| After Hydrogenation | | | | | | |
| Example | $H_2$ Concentration | | | | | |
| A | 80 ppm | 650 | 6 | 2 | 47.1 | −2.7 |
| B | 150 ppm | 43 | 1 | 1 | 44.3 | −8.3 |

Δc is the relative change in butene-1 concentration, based on its concentration before hydrogenation.

In both cases, butadiene, butyne, and butenyne are not completely hydrogenated although, with an excess of $H_2$ of about 100% based on the stoichiometric quantity, a larger portion of these compounds is hydrogenated.

The butene-1 concentration is markedly decreased in both cases during hydrogenation; a portion of butene-1 is hydrogenated to butane or isomerized to butene-2. Both of these occurrences are disadvantageous to the production of butene-1.

TABLE 1

Composition of the HC Mixtures Employed in Examples A, B, and 1-22

|  | Concentration of the Compounds | | | | |
|---|---|---|---|---|---|
| HC Mixture Employed for Example | A, B 1-5 21 | 6-8 9-12 18-20 | 13-17 | 22 | Unit Conc. |
| Propane |  |  |  | 1.2 | % |
| Propene |  |  |  | 0.3 | % |
| Propadiene |  |  |  | 0.180 | % |
| Propyne (Methylacetylene) |  |  |  | 0.620 | % |
| Isobutane | 0.028 | 0.032 | 0.040 | 0.130 | % |
| n-Butane | 21.5 | 21.6 | 22.2 | 13.0 | % |
| Isobutene | 0.072 | 0.082 | 0.110 | — | % |
| Butene-1 | 48.4 | 48.2 | 53.9 | 37.4 | % |
| cis-Butene-2 | 14.2 | 14.1 | 8.8 | — | % |
| trans-Butene-2 | 15.6 | 15.5 | 14.7 | 26.8 | % |
| 1,3-Butadiene | 0.196 | 0.514 | 0.261 | 19.5 | % |
| 1,2-Butadiene | — | — | — | 0.073 | % |
| 1-Butyne (Ethylacetylene) | 0.0056 | 0.0056 | 0.0030 | 0.058 | % |
| Butenyne (Vinylacetylene) | 0.0012 | 0.0012 | 0.0012 | 0.512 | % |
| HC of 5 and More Carbon Atoms |  |  |  | 0.2 | % |
| Stoichiometric $H_2$ Concentration | 76 | 194 | 101 | 8135 | ppm |

TABLE 2

Composition of the HC Mixtures Utilized in Examples 23 and 24

|  | Concentration of the Compounds | | |
|---|---|---|---|
| HC Mixture Utilized for Example | 23 | 24 | Unit Conc. |
| Propane | 6.35 |  | % |
| Propene | 93.3 |  | % |
| Propadiene | 0.21 |  | % |
| Propyne (Methylacetylene) | 0.15 |  | % |
| Stoichiometric $H_2$ Concentration | 182 |  | ppm |
| Pentanes |  | 5.68 | % |
| Pentenes |  | 81.9 | % |
| Isoprene |  | 12.4 | % |
| Stoichiometric $H_2$ Concentration |  | 3680 | ppm |

EXAMPLES 1-5

Influence of Reaction Temperature and CO Concentration on Hydrogenation

In the hydrocarbon mixture of Table 1, 85 ppm of $H_2$; i.e., somewhat more than the stoichiometric $H_2$ quantity (76 ppm) and the variable minimum CO quantity, adapted to the hydrogenation temperature, are dissolved. The hydrocarbon mixture (water content < 5 ppm) is hydrogenated under the following conditions:

Temperature variable
Throughput 35 liter/liter·hour
Pressure 1.3 MPa
Catalyst 0.5% Pd on Al₂O₃
The following result was obtained:

|  |  |  | HC Mixture Contains | | | |
|---|---|---|---|---|---|---|
|  |  |  | Butadiene ppm | Butyne ppm | Butenyne ppm | Butene-1 % |
| Before Hydrogenation | | | 1960 | 56 | 12 | 48.4 |
| After Hydrogenation | | | | | | |
| Example | Temperature °C | Concentration CO ppm | | | | |
| 1 | 5 | 0.4 | 2 | <1 | <1 | 48.5 |
| 2 | 21 | 0.6 | 3 | <1 | <1 | 48.5 |
| 3 | 41 | 1.8 | 1 | <1 | <1 | 48.5 |
| 4 | 55 | 4.2 | 2 | <1 | <1 | 48.5 |
| 5 | 75 | 10.0 | 1 | <1 | <1 | 48.4 |

Butadiene, butyne, and butenyne are practically completely hydrogenated in the entire temperature range by using the indicated concentration of dissolved CO. The minimum CO concentration rises greatly in the temperature range examined.

In contrast to the comparative examples, the butene-1 concentration does not decrease but rather remains practically unchanged as well as the concentration of n-butane, iso-butene, cis-butene-2 and trans-butene-2 mentioned in Table 1. This result is in accordance with the very low excess of hydrogen.

EXAMPLES 6-8

Influence of CO Concentration on Hydrogenation Selectivity at Elevated Reaction Temperature In the hydrocarbon mixtures shown in Table 1, 210 ppm of H₂; i.e., somewhat more than the stoichiometric amount of H₂ (194 ppm) and a variable amount of CO are dissolved. The hydrocarbon mixture (water content <5 ppm) is hydrogenated under the following conditions:
Temperature 55° C.
Throughput 35 liter/liter·hour
Pressure 1.3 MPa
Catalyst 0.5% Pd on Al₂O₃
The following result was obtained:

|  |  | HC Mixture Contains | | | |
|---|---|---|---|---|---|
|  |  | Butadiene ppm | Butyne ppm | Butenyne ppm | Butene-1 % |
| Before Hydrogenation | | 5140 | 52 | 12 | 48.2 |
| After Hydrogenation | | | | | |
| Example | Concentration CO ppm | | | | |
| 6 | 4.2 | 4 | <1 | <1 | 48.4 |
| 7 | 1.8 | 100 | <1 | <1 | 48.2 |
| 8 | 0.6 | 250 | <1 | <1 | 47.5 |

Under these hydrogenation conditions, the CO concentration of 4.2 ppm is the minimum concentration. The CO concentrations of 1.8 ppm and 0.6 ppm are, clearly, lower than the minimum concentration; in both examples, butadiene is not hydrogenated completely, while butyne and butenyne experience complete hydrogenation. The butene-1 concentration is lower in Examples 7 and 8 than in Example 6.

EXAMPLES 9-12

Influence of CO Concentration on Hydrogenation Selectivity at a Low Reaction Temperature Analogously to Examples 6-8, again 210 ppm of H₂; i.e., somewhat more than the stoichiometric H₂ quantity (194 ppm) and a variable amount of CO are dissolved in the hydrocarbon mixture of Table 1. The hydrocarbon mixture is hydrogenated under the following conditions:
Temperature 21° C.
Throughput 35 liter/liter·hour
Pressure 1.3 MPa
Catalyst 0.5% Pd on Al₂O₃
The following results were obtained:

|  |  | HC Mixture Contains | | | |
|---|---|---|---|---|---|
|  |  | Butadiene ppm | Butyne ppm | Butenyne ppm | Butene-1 % |
| Before Hydrogenation | | 5140 | 52 | 12 | 48.2 |
| After Hydrogenation | | | | | |
| Example | Concentration CO ppm | | | | |
| 9 | 0.1 | 780 | <1 | <1 | 47.3 |
| 10 | 0.4 | 230 | <1 | <1 | 47.8 |
| 11 | 0.6 | 1 | <1 | <1 | 48.3 |
| 12 | 1.8 | 2 | <1 | <1 | 48.4 |

Under these hydrogenation conditions, 0.6 ppm of CO is the minimum concentration. Values of 0.1 ppm and 0.4 ppm are clearly too small; in both cases, butadiene is not completely hydrogenated, and the butene-1 concentration is lower after hydrogenation than before. No advantage is obtained with 1.8 ppm of CO as compared with the minimum concentration in Example 11.

EXAMPLES 13-17

Determination of Minimum CO Quantity

A variable amount of CO and a variable amount of H₂ are dissolved in a hydrocarbon mixture as shown in Table 1; the amount of H₂ is in most cases larger than the required stoichiometric quantity (101 ppm). The mixture is hydrogenated under the following conditions:
Temperature 40° C.
Throughput 21 liter/liter·hour
Pressure 1.3 MPa
Catalyst 0.5% Pd on activated carbon
The following results were achieved:

|  |  |  |  | HC Mixture Contains | | | |
|---|---|---|---|---|---|---|---|
|  |  |  |  | Butadiene ppm | Butyne ppm | Butenyne ppm | Butene-1 % |
| Before Hydrogenation | | | | 2610 | 30 | 25 | 53.9 |
| After Hydrogenation | | | | | | | |
| Example | CO ppm | H₂ ppm | E % | | | | |
| 13 | 1.7 | 105 | 4 | 2 | <1 | <1 | 54.0 |
| 14 | 1.7 | 150 | 49 | 3 | <1 | <1 | 53.5 |
| 15 | 3.4 | 150 | 49 | 2 | <1 | <1 | 53.9 |
| 16 | 1.7 | 180 | 78 | 2 | <1 | <1 | 52.9 |
| 17 | 7.0 | 180 | 78 | 4 | <1 | <1 | 53.9 |

E is the relative excess over the stoichiometric quantity.

The CO concentration of 1.7 ppm is adequate if no excess of $H_2$ is employed; in contrast thereto, this concentration is too low if the $H_2$ excess is 49%. On the other hand, 3.4 ppm of CO at a 49% $H_2$ excess are indeed sufficient. With an excess of 78% $H_2$, 7.0 ppm of CO are required.

Within the range of complete solubility of $H_2$ there is no upper limit as to the amount of hydrogen. Increasing the excess of $H_2$ and keeping CO at its minimum concentration results in the same selectivity as in case of small excess of $H_2$. Therefore there is no reason to increase the concentration of $H_2$ too much.

EXAMPLES 18-20

Relationship Between CO Concentration and Reaction Pressure

In the hydrocarbon mixture shown in Table 1, 205 ppm of $H_2$; i.e., somewhat more than the required stoichiometric $H_2$ quantity (194 ppm) and 0.6 ppm of CO are dissolved. The mixture is hydrogenated under the following conditions:
Temperature 21° C.
Throughput 35 liter/liter·hour
Pressure variable
Catalyst 0.5% Pd on $Al_2O_3$
The following results were obtained:

|  |  | HC Mixture Contains | | | |
|---|---|---|---|---|---|
|  |  | Butadiene ppm | Butyne ppm | Butenyne ppm | Butene-1 % |
| Before Hydrogenation |  | 5140 | 56 | 12 | 48.2 |
| After Hydrogenation |  |  |  |  |  |
| Example | Pressure MPa |  |  |  |  |
| 18 | 1.0 | 2 | <1 | <1 | 48.5 |
| 19 | 1.5 | 1 | <1 | <1 | 48.4 |
| 20 | 1.8 | 3 | <1 | <1 | 48.5 |

The pressure at which the mixture is hydrogenated has, in the range under investigation, practically no effect on the result of the hydrogenation. Measured by the butene-1 concentration, the CO concentration is practically independent of the reaction pressure.

EXAMPLE 21

Influence of the Water Content on Minimum CO Quantity $H_2$ and CO were dissolved in the mixture shown in Table 1 and the water concentration was varied. The mixture was hydrogenated under the following conditions:
Temperature 21° C.
Throughput 35 liter/liter·hour
Pressure 1.3 MPa
Catalyst 0.5% Pd on $Al_2O_3$
At 300 ppm of water, complete hydrogenation of butadiene, butyne, and butenyne is achieved with a markedly lower CO concentration than at about 5 ppm of water.

|  |  |  | HC Mixture Contains | | | |
|---|---|---|---|---|---|---|
|  |  |  | Butadiene ppm | Butyne ppm | Butenyne ppm | Butene-1 % |
| Before Hydrogenation |  |  | 1960 | 56 | 12 | 48.4 |
| After Hydrogenation |  |  |  |  |  |  |
|  | Concentration | | | | | |
| Example | $H_2$ ppm | CO ppm | $H_2O$ ppm |  |  |  |
| 2 | 85 | 0.6 | <5 | 3 | <1 | <1 | 48.4 |
| 21 | 80 | 0.3 | 300 | 2 | <1 | <1 | 48.5 |

By using the stoichiometric $H_2$ concentration of 76 ppm, the same result is obtained within the detection accuracy.

EXAMPLE 22

Selective Hydrogenation with High Concentration of Polyunsaturated Hydrocarbons

The mixture shown in Table 1 with about 21% of compounds to be hydrogenated requires the stoichiometric quantity of 8135 ppm of $H_2$ in the hydrogenation of the polyunsaturated $C_4$-compounds to butene and the polyunsaturated $C_3$-compounds to propene. In this hydrocarbon mixture, 1 ppm of CO is dissolved. The mixture is first introduced into a recycling reactor. 7980 ppm of $H_2$ is fed into the recycle stream—based on the freshly introduced mixture—and homogeneously dissolved therein. The hydrogen-containing mixture is hydrogenated in the cycle at 25° C. and 1.3 MPa on a catalyst with 0.5% Pd on $Al_2O_3$. The ratio of recycled quantity to introduced quantity is 49:1. The total throughput in the recycling reactor is 68 liter/liter·hour. Another 250 ppm of $H_2$ is dissolved in the mixture withdrawn from the recycle reactor, and the mixture is rehydrogenated in a secondary reactor at 25° C. and 1.3 MPa with 27 liter/liter·hour. No additional CO is introduced upstream of the secondary reactor.

The following result was thus achieved:

| HC Mixture Contains | Before Hydrogenation ppm | After Hydrogenation | |
|---|---|---|---|
|  |  | At Outlet of Recycle Reactor ppm | At Outlet of Secondary Reactor ppm |
| Butadiene | 195,730 | 4,710 | 2 |
| Butyne | 580 | 4 | <1 |
| Butenyne | 5,120 | 2 | <1 |
| Propadiene | 1,800 | 270 | <1 |
| Propyne | 6,200 | 8 | <1 |

The butene-1 concentration increased from 37.4% to 48.6%, the propene concentration from 0.3% to 1.1%.

According to the process of this invention, a proportion of about 21% of polyunsaturated compounds is likewise selectively hydrogenated.

EXAMPLE 23

Selective Hydrogenation of a $C_3$-Hydrocarbon Mixture

In the hydrocarbon mixture of Table 2, 195 ppm of $H_2$; i.e., somewhat more than the stoichiometric $H_2$ quantity (182 ppm) and 2.5 ppm of CO are dissolved. The hydrocarbon mixture is hydrogenated under the following conditions:
Temperature 45° C.
Throughput 40 liter/liter·hour
Pressure 3.0 MPa
Catalyst 0.1% Pd on $Al_2O_3$ The following was the result:

|  | HC Mixture Contains | | |
|---|---|---|---|
|  | Propadiene ppm | Propyne ppm | Propene % |
| Before Hydrogenation | 2,100 | 1,500 | 93.3 |
| After Hydrogenation | 3 | <1 | 93.6 |

Therefore, propadiene and propyne have been quantitatively hydrogenated to propene.

EXAMPLE 24

Selective Hydrogenation of a $C_5$-Hydrocarbon Mixture

The hydrocarbon mixture according to Table 2 with about 12% of compounds to be hydrogenated requires the stoichiometric quantity of 3680 ppm of $H_2$ in the hydrogenation of the polyunsaturated $C_5$-compounds to pentenes. In this mixture, 1.2 ppm of CO is dissolved. The hydrocarbon mixture is introduced into a recycling reactor at 28° C. and 1.8 MPa. 3800 ppm of $H_2$ is fed into the recycle stream—based on the freshly introduced mixture—and homogeneously dissolved therein. The hydrogen-containing mixture is hydrogenated on a catalyst with 2.0% Pd on $Al_2O_3$ with a total throughput of 23 liter/liter·hour. The ratio of recycled quantity to introduced quantity is 26:1. The throughput of freshly fed mixture is 0.9 liter/liter·hour. Without additional hydrogenation in a secondary reactor, the following result was obtained:

|  | HC Mixture Contains | |
|---|---|---|
|  | Isoprene ppm | Pentene % |
| Before Hydrogenation | 124,000 | 81.9 |
| After Hydrogenation | 30 | 94.3 |

Isoprene has, thus, been quantitatively hydrogenated in a selective fashion.

What is claimed is:

1. A process for the selective hydrogenation of hydrocarbons having conjugated double bonds, cumulative double bonds or acetylenic triple bonds or combinations thereof in a monoene-containing mixture of hydrocarbons having at least three carbon atoms in the liquid phase on a fixed catalyst on an inert support, which comprises:

adding hydrogen to the hydrocarbon mixture to be hydrogenated, in a finely divided form and in such quantitative ratios that the hydrogen is completely dissolved in the hydrocarbon mixture and a homogeneous liquid phase is obtained before the hydrocarbon mixture enters a hydrogenation zone, said hydrogen being added in an amount from once to twice the stoichiometric quantity for effecting the hydrogenation of the polyunsaturated and acetylenic compounds to the corresponding monoenes;

adding carbon monoxide to the hydrocarbon mixture to be hydrogenated, in a finely divided form, wherein the carbon monoxide is completely dissolved in the hydrocarbon mixture and a homogeneous liquid phase is obtained before the hydrocarbon mixture enters the hydrogenation zone, and wherein the proportion of carbon monoxide amounts to at least 0.05 ppm by weight based on the weight of the hydrocarbon mixture; and passing the resulting reaction mixture in the liquid phase over a fixed catalyst containing 0.01 to 3% by weight of palladium, based on the weight of the support in a hydrogenation zone maintained at the reaction conditions required for effecting selective hydrogenation whereby the content of hydrocarbons having conjugated double bonds cumulative double bonds or acetylenic triple bonds or combinations thereof is reduced by said selective hydrogenation.

2. A process according to claim 1, wherein carbon monoxide is added in an amount of between 0.05 and 20 ppm by weight of the hydrocarbon mixture.

3. A process according to claim 1, wherein the reaction mixture is passed over a catalyst containing by weight of 0.1-2% palladium on an inert aluminum oxide.

4. A process according to claim 1, wherein the reaction conditions include a temperature between 0° C. and 75° C. during hydrogenation.

5. A process according to claim 1, wherein said monoene-containing mixture of hydrocarbons is a mixture containing a monoene having three, four, or five carbon atoms, or a mixture containing monoenes with three to five carbon atoms.

6. A process according to claim 1, wherein the monoene in said monoene-containing mixtures is butene-1.

7. A process according to claim 1, wherein the hydrocarbon mixture to which hydrogen and carbon monoxide are added contains minor amounts of diolefinic hydrocarbons including butadiene and acetylenes and a major amount of a monoene-containing mixture of hydrocarbons comprising propene, butene and isobutene and the reaction product contains less than 5 ppm of butadiene and less than 1 ppm of the diolefinic and acetylenic hydrocarbons.

8. A process according to claim 1, wherein the hydrogen added to the hydrocarbon mixture has a concentration below 1%.

9. A process according to claim 1, wherein the hydrocarbons having conjugated and/or cumulative double bonds or acetylene triple bonds or combinations thereof are hydrogenated to form monoene-containing hydrocarbons.

10. A process according to claim 1, wherein the throughput of the hydrocarbon mixture to be subjected to hydrogenation in a reactor is in a range of 5 to 300 liters of hydrocarbon mixture per liter of catalyst volume per hour.

11. A process according to claim 1, wherein the reaction conditions include a reaction pressure not in excess of 6 MPa.

12. A process according to claim 11, wherein said reaction conditions include a temperature of from 0° C. to about 90° C.

* * * * *